US007341734B2

(12) United States Patent
Gillies et al.

(10) Patent No.: US 7,341,734 B2
(45) Date of Patent: Mar. 11, 2008

(54) PERSONAL CARE COMPOSITIONS COMPRISING SEMICONDUCTOR NANOCRYSTALS AND METHODS OF MAKING AND USING THE SAME

(75) Inventors: Jennifer Gillies, Petersburg, NY (US); Margaret Hines, Troy, NY (US)

(73) Assignee: Evident Technologies, Troy, NY (US)

( * ) Notice: Subject to any disclaimer, the term of this patent is extended or adjusted under 35 U.S.C. 154(b) by 159 days.

(21) Appl. No.: 11/283,903

(22) Filed: Nov. 22, 2005

(65) Prior Publication Data

US 2006/0134029 A1 Jun. 22, 2006

Related U.S. Application Data

(60) Provisional application No. 60/630,177, filed on Nov. 23, 2004.

(51) Int. Cl.
*A61K 8/00* (2006.01)
*A61K 8/19* (2006.01)
*A61K 8/23* (2006.01)
*A61K 8/26* (2006.01)
*A61K 8/27* (2006.01)

(52) U.S. Cl. .......................... 424/401; 424/59; 424/64; 424/70.1; 424/600; 424/601; 424/604; 424/641; 424/650; 424/654; 424/682; 424/702; 424/703; 424/718

(58) Field of Classification Search ................ 424/401, 424/600, 702, 703, 718
See application file for complete search history.

(56) References Cited

U.S. PATENT DOCUMENTS 5,417,961 A * 5/1995 Nearn et al. ................. 424/59
2003/0215522 A1* 11/2003 Johnson et al. ............. 424/642

* cited by examiner

*Primary Examiner*—Johann Richter
*Assistant Examiner*—Konata M. George
(74) *Attorney, Agent, or Firm*—Kenyon & Kenyon LLP

(57) ABSTRACT

A personal care composition that includes a personal care ingredient and semiconductor nanocrystals. A method of protecting at least a portion of a body against ultraviolet radiation by applying a personal care composition is also provided.

16 Claims, 4 Drawing Sheets

Absorbtion Spectrum of ZnSe Semiconductor Nanocrystal Complex

Absorbtion Spectrum of ZnSe Semiconductor Nanocrystal Complex

PERSONAL CARE COMPOSITIONS COMPRISING SEMICONDUCTOR NANOCRYSTALS AND METHODS OF MAKING AND USING THE SAME

CROSS-REFERENCE TO RELATED APPLICATIONS

The present application claims priority to U.S. Provisional Application No. 60/630,177, filed Nov. 23, 2004, which is incorporated by reference herein.

FIELD OF THE INVENTION

The present application relates to personal care compositions comprising semiconductor nanocrystals and methods of making the same. The present invention also relates to methods of protecting at least a portion of a body against ultraviolet radiation.

BACKGROUND OF THE INVENTION

Concerns about the health and materials degradation impacts of ultraviolet (UV) radiation are being raised with increasing frequency. UV radiation from the sun can cause skin cancers, eye problems, and can degrades light-sensitive artifacts. Traditional chemical sunscreens act primarily by binding to skin protein and absorbing UVB (280-320 nm) photons. The majority of these sunscreens are based on para-aminobenzoic acid, cinnamates such as methoxycinnamate, and various salicylates. Although these substances tend to absorb strongly in the UVB range, many of these substances do not absorb sunlight strongly in the UVA range (320-400 nm). Many commercial preparations are weak UVB/UVA absorbers, including benzophenones, dibenzoylmethanes, and anthraline derivatives, which have a limited UVA absorption as well. Octocrylene is a weak but stable UVB absorber used to protect other agents from degrading. Avobenzone (Parsol-1789) is a benzophenone with fair UVA protection, but it degrades readily and tends to cause irritation when applied to the skin. All of these organic sunscreens can cause allergic or irritant contact dermatitis, photoxic, and photoallergic reactions and no single organic agent gives complete protection from UVA and UVB radiation.

In addition to organic agents, inorganic agents, often referred to as sunblocks, act as barriers by reflecting or scattering radiation. These physical blockers include metal oxide compounds such as iron, zinc, titanium and bismuth. Iron oxide pigments are incorporated in many personal care products, and provide protection from not only UV radiation, but visible and IR (infrared) radiation as well. Zinc Oxide (ZnO) and Titanium Dioxide ($TiO_2$) are highly reflective white powders. In the personal care product industry, bulk inorganic UV absorbers such as ZnO and TiO2 have been used for many years to protect people from the effects of UV radiation. Inorganic UV absorbers have many desirable characteristics such as a long history of topical use, low irritancy, broad spectrum absorption and high photo-stability. Zinc oxide, being inorganic, is photostable and thus as opposed to the majority of organic absorbers, its effectiveness as a UV absorber is not lessened over time with sunlight exposure. However, rather than absorbing UV radiation, ZnO, $TiO_2$ and other inorganic components of personal care products are typically used to scatter light. The scattering of light by these inorganic particles causes a whitening effect on a users skin once applied which leads to poor cosmetic appeal. Thus, the recognized value of ZnO as an acceptable UV skin protector is decreased due to this whitening effect.

An additional problem associated with inorganic components of sunscreen is that they often do not disperse well in many personal care ingredients. Additionally, inorganic absorbers due to their relatively large particle size may lead to aggregation.

There is a need for a UV absorber that does not have the whitening effect typical of inorganic UV absorbers and that are soluble in and may be dispersed evenly in oily skin lotions.

SUMMARY OF THE INVENTION

In an embodiment, the present invention provides a personal care composition comprising a personal care ingredient and a semiconductor nanocrystal dispersed or dissolved in the personal care ingredient.

In an embodiment, the present invention provides a personal care composition comprising a personal care ingredient and a matrix material comprising a semiconductor nanocrystal, wherein the matrix material is dispersed or dissolved in the personal care ingredient.

In another embodiment, the present invention provides a method of protecting at least a portion of a body against ultraviolet radiation. The method comprises applying to the at least a portion of the body a personal care composition comprising a personal care ingredient and a semiconductor nanocrystal.

DETAILED DESCRIPTION OF THE INVENTION

In embodiments, the present invention provides personal care compositions comprising a personal care ingredient and a semiconductor nanocrystal. A personal care composition can be any type of personal care product such as, for example, a hair conditioner; moisturizer; sun tan lotion; make-up such as lipstick; or hair gel.

A personal care ingredient is an ingredient that is typically used in the production of a personal care product. Non-limiting examples of personal care ingredients include fatty acids; fatty esters; waxes; oils; triglycerides; long chain alcohols; silicones; and emulsions such as water and oil, oil and wax, wax and water; silicone; antiseptics; astringents; and any combinations thereof. Fatty acids and esters may be used in cosmetics as emollients, thickening agents, and cleansing agents, when mixed with glycerin. Waxes have many uses in personal care applications as thickening and emollient agents, specifically, waxes may be used as a lipsticks or stick foundations. Oils such as almond oil, Echium lycopsis oil, arachidic oil, castor oil, hazelnut oil, plam oil and coconut oil may be used as an emollient.

Additionally, many oils, such as Echium lycopsis oil, have potent antioxidant properties and apricot oil, canola oil, coconut oil, corn oil, jojoba oil, jojoba wax, lanolin, lecithin, olive oil, safflower oil, sesame oil, shea butter, soybean oil, squalane, and sweet almond mimic the lipid content of the skin which can assist in the moisturizing of skin. Mineral oil is often used in cosmetics because it does not form a solid and clog pores. Triglycerides, such as glyceryl ester are often emollient and thickening agent in cosmetics. For personal care applications, alcohols as a group of organic compounds have a large range of forms and uses. For example, they are glycols that can be used as humectants that deliver ingredients into skin. Additionally, when fats and oils are chemically reduced, they may become fatty alcohols which can be used as an emollient or cleansing agent.

Figure 1:
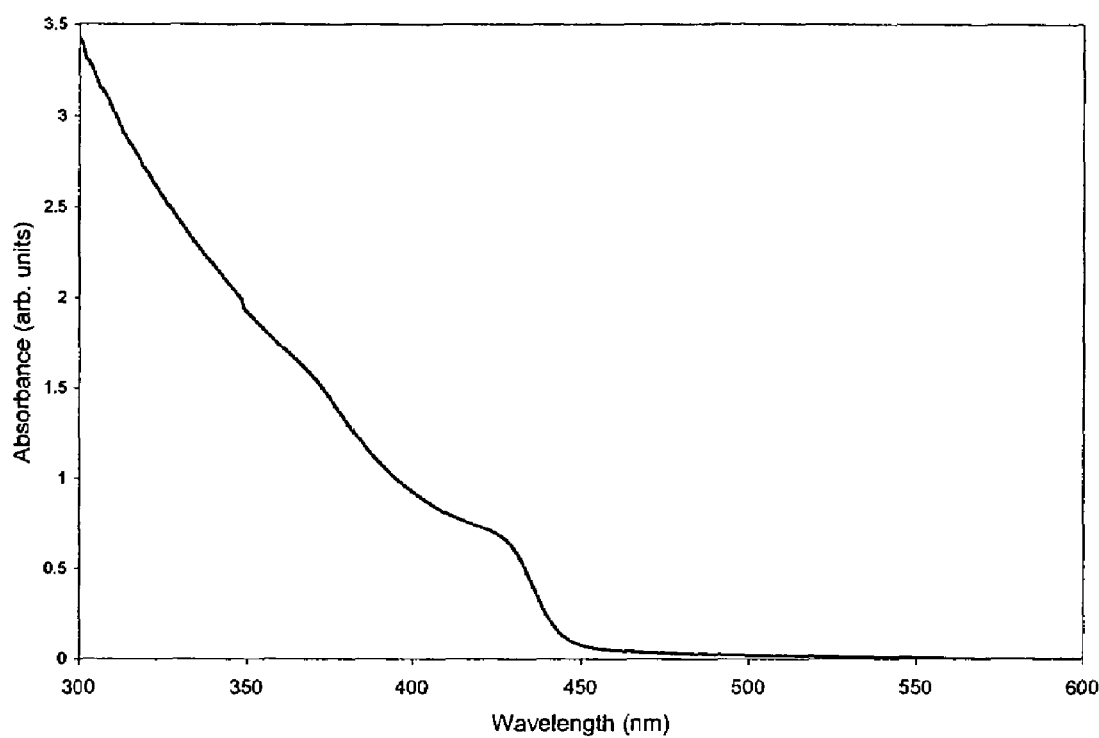
FIG. 1 represents an absorption spectrum of an example zinc selenide semiconductor nanocrystal.

A semiconductor nanocrystal is typically a tiny crystal of II-VI, III-V, IV-VI material that has a diameter typically between 1 nm and 20 nm. In the strong confinement limit, the physical diameter of the nanocrystal is smaller than the bulk exciton Bohr radius causing quantum confinement effects to predominate. In this regime, the nanocrystal is a 0-dimensional system that has both quantized density and energy of electronic states where the actual energy and energy differences between electronic states are a function of both the nanocrystal composition and physical size. Larger nanocrystals have more closely spaced energy states and smaller nanocrystals the reverse. Because interaction of light and matter is determined by the density and energy of electronic states, many of the optical and electric properties of nanocrystals can be tuned or altered simply by changing the nanocrystal geometry (i.e. physical size). Thus, the absorbance properties of the nanocrystals in the present invention may be tuned to optimize the particular wavelength of light desired to be absorbed. Non-limiting examples of semiconductor nanocrystals that can be used in embodiments of the present invention include ZnSe, ZnS, ZnO, CdS, SrS, SrSe, GaN, InN, GaP, and AlP. All of these semiconductor nanocrystals have been shown to strongly absorb in the UV range. For example, FIG. 1 represents an absorption spectrum of an example zinc selenide semiconductor nanocrystal. This spectrum shows strong absorbance of both UV A and UV B light. Specifically, this spectrum of ZnSe strongly absorbs LV light with a wavelength less than 400 nm. Additionally, many other semiconductor nanocrystals may be used that can also strongly absorb in the UV range. By including a semiconductor nanocrystal in a personal care composition in accordance with embodiments of the present invention, the personal care composition can exhibit some of the absorbance properties of the underlying semiconductor nanocrystal.

In an exemplary embodiment, a personal care composition comprises a semiconductor nanocrystal dispersed or dissolved directly into a personal care ingredient. In another exemplary embodiment, a personal care composition comprises a personal care ingredient and a matrix material comprising a semiconductor nanocrystal, wherein the matrix material is dispersed or dissolved in the personal care ingredient. Non-limiting examples of matrix materials include polymers and silica sol-gels, polystyrenes, silicon based polymers, polyacrylates, polyurethanes, and polycarbonates as well as other polymers and any combinations thereof.

Figure 2:
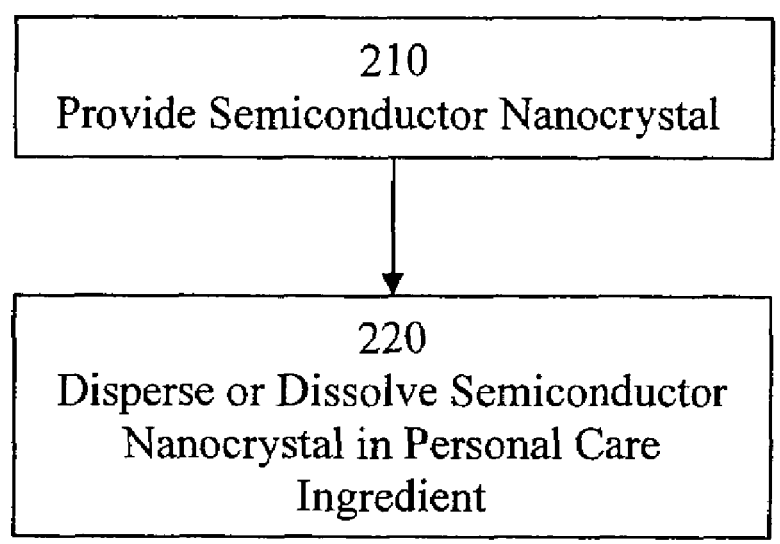
FIG. 2 is a flow chart of a method of making a personal care composition according to an embodiment of the present invention.

The present invention also provides methods of manufacturing personal care compositions. Referring to FIG. 2, in an embodiment, a method of manufacturing a personal care composition comprises providing semiconductor nanocrystals by preparing or otherwise obtaining semiconductor nanocrystals (step 210). Semiconductor nanocrystals may be prepared using any known method of semiconductor nanocrystal preparation. Alternatively, semiconductor nanocrystals suitable in the present invention can be otherwise obtained by purchasing semiconductor nanocrystals (Evident Technologies, Troy, N.Y.). The method further comprises dispersing or dissolving the semiconductor nanocrystals in a personal care ingredient by stirring, shaking or other suitable mixing techniques (step 220).

Figure 3:
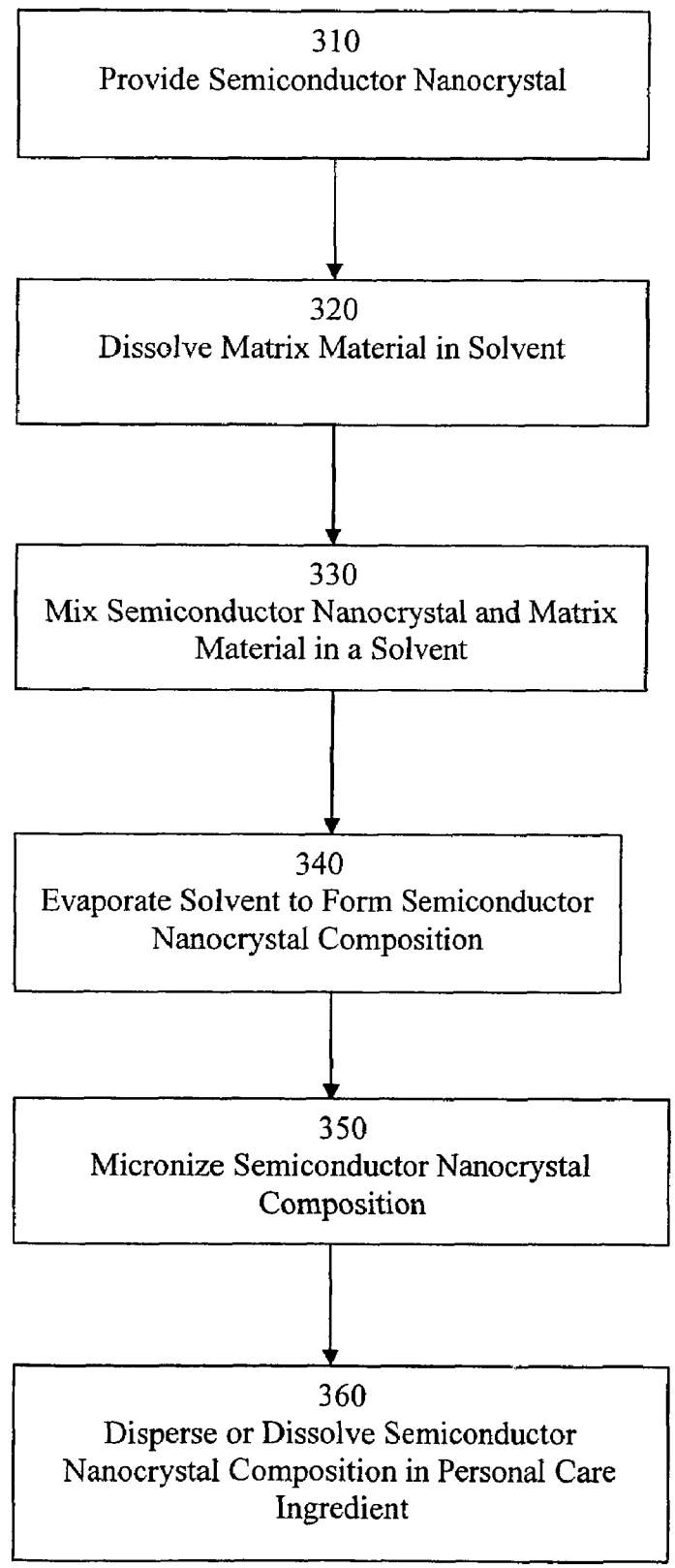
FIG. 3 is a flow chart of a method of making a personal care composition according to an embodiment of the present invention.

Referring to FIG. 3, in another embodiment, a method of manufacturing a personal care composition comprises providing semiconductor nanocrystals by preparing or otherwise obtaining semiconductor nanocrystals (step 310) as described above. Generally, the semiconductor nanocrystals are purchased or prepared in a solution. In step 320, a matrix material is dissolved in the same type of solvent that the semiconductor nanocrystals are purchased or prepared in, for example toluene. Examples of matrix materials that may be dissolved in toluene, a common solvent used in the preparation of semiconductor nanocrystals, include polystyrenes, silicon based polymers, polyacrylates, polyurethanes, and polycarbonates as well as other polymers. The matrix material may be dissolved in the solvent, toluene, by heating the solvent, approximately, 110° C. until the matrix material is dissolved. It is appreciated that the temperature indicated for dissolving the matrix material is only exemplary and the proper temperature and time to dissolve may depend on the initial size of the matrix material, the temperature, as well as the type of matrix material used.

In step 330, the semiconductor nanocrystal solution provided in step 310 is added to the solution comprising the matrix material dissolved in the same solvent. This mixing step results in the semiconductor nanocrystals and a matrix material dissolving in a common solvent. First mixing the semiconductor nanocrystals in a matrix material can hermetically seal the semiconductor nanocrystal from the environment.

In step 340, the solvent is evaporated out of the solution leaving a solid semiconductor nanocrystal composition comprising semiconductor nanocrystals in the matrix material. Initially, the solvent can evaporated by heating the solution to 110° C., for example. The solution can then be poured in tray and placed in a fume hood. Evaporation can continued until the solution prepared in step turns into a solid semiconductor nanocrystal composition.

In step 350, the solid semiconductor nanocrystal composition is micronized or ground until it is the desired size. Initially, the semiconductor nanocrystal composition can be blended to reduce the size of the semiconductor nanocrystals and make it easier to micronize the particles. The desired size of the particles can vary depending on the application. Additionally, size of the particles may be larger or smaller as desired in the given application.

In step 360, the semiconductor nanocrystal composition is dispersed or dissolved in a personal care ingredient. For example the semiconductor nanocrystal composition can be dispersed or dissolved in fatty acids, fatty esters, waxes, oils, triglycerides, long chain alcohols, and silicones. These materials are commonly used in the preparation of personal care products and directly dispersing or dissolving semiconductor nanocrystals in these materials allows for these materials to absorb light in the UV range. The micronized (or sub-micronized) semiconductor nanocrystal composition can be mixed into a personal care ingredient by using vigorous stirring, shaking, or other suitable mixing techniques.

Figure 4:
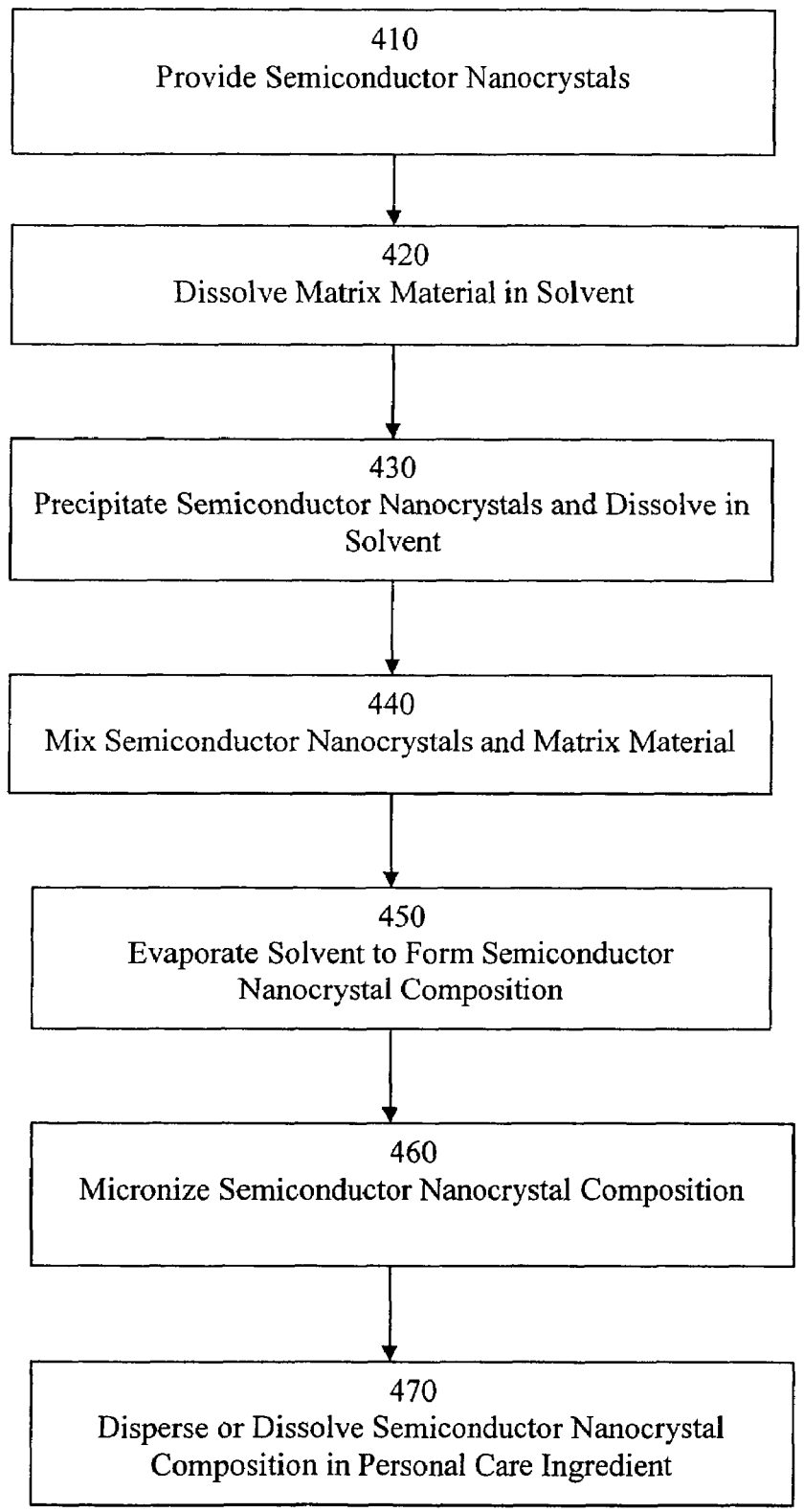
FIG. 4 is a flow chart of a method of making a personal care composition according to an embodiment of the present invention.

Referring to FIG. 4, in another embodiment, the present invention provides a method of manufacturing a personal care composition comprising providing a semiconductor nanocrystal (step 410), as described above. For the purpose of the procedure described below, the semiconductor nanocrystals prepared and/or purchased is dissolved in a solution, such as toluene, for example.

In step 420, a matrix material is dissolved in a solvent. For the purpose of this exemplary embodiment, the matrix material is not soluble in the solvent in which the semiconductor nanocrystal in step 410 is provided. Thus, it is necessary to find a solvent that will dissolve both the semiconductor nanocrystals prepared in toluene, for example, and the matrix material. Non-limiting examples of solvents that have been found to dissolve semiconductor nanocrystals and typical matrix materials include anisole, chloroform, hexane, and tetrachloroethylene. The matrix material can be dissolved in the solvent by heating the solvent to, approximately, 110° C. until the matrix material is dissolved. It is appreciated that the temperature indicated for dissolving the matrix material is only exemplary and the proper temperature and time to dissolve may depend on the initial size of the matrix material, the temperature, as well as the type of matrix material used.

In step 430, the semiconductor nanocrystals provided in step 410 are precipitated out of solution and dissolved in the solvent containing the matrix material. The semiconductor nanocrystal may be precipitated out of the solution by adding methanol to the solution. Once, the majority of semiconductor nanocrystals have been precipitated out of the solution, the solution can be centrifuged. The resulting liquid containing methanol and the original solvent in which the semiconductor nanocrystals were prepared in step 410, can be discarded leaving the semiconductor nanocrystals. The semiconductor nanocrystals can then be dissolved in the solution containing the matrix material.

In step 440, the resulting semiconductor nanocrystals dissolved in the solvent from step 430 is added to the solution which contains the dissolved matrix material. The resulting semiconductor nanocrystal-matrix material solvent solution is mixed. Because the semiconductor nanocrystals and the matrix material are both able to dissolve in the solvent, the addition of the semiconductor nanocrystals to the solution allows for the semiconductor nanocrystals to mix homogeneously with the matrix material. Mixing can occur by a simple stirring of the solution.

In step 450, the solvent is evaporated out of the solution leaving a solid semiconductor nanocrystal composition comprising semiconductor nanocrystals in the matrix material. Initially, the solvent may be evaporated by heating the solution to 110° C. The solution may then be poured in tray and placed in a fume hood. Evaporation is continued until the solution prepared in step 440 turns into a solid semiconductor nanocrystal composition.

In step 460, the semiconductor nanocrystal composition is micronized or ground into particles of submicron size. Initially, the semiconductor nanocrystal composition can be blended to reduce the size of the semiconductor nanocrystals and make it easier to micronize the particles. The desired size of the particles may vary depending on the application. It has been found that the particles may be micronized from anywhere between 0.5 microns to 100 microns. The micronization may take place by known micronization techniques. Additionally, size of the particles may be larger or smaller as desired in the given application.

In step 470, the semiconductor nanocrystal composition is dispersed or dissolved in a personal care ingredient, as described above.

In another embodiment, the present invention provides a method of protecting at least a portion of a body against ultraviolet radiation comprising applying to the portion of the body a personal care composition comprising a personal care ingredient and a semiconductor nanocrystal. The personal care composition can include any of the above-referenced personal care compositions. For example, the personal care composition according to a method of the present invention can comprise a personal care ingredient and a semiconductor nanocrystal dissolved or dispersed in the personal care ingredient. Alternatively, the personal care composition can comprise a personal care ingredient and a matrix material comprising a semiconductor nanocrystal, wherein the matrix material is dispersed or dissolved in the personal care ingredient. As described above, the personal care composition can be any type of personal care product such as, for example, a hair conditioner; moisturizer; sun tan lotion; make-up such as lipstick; or hair gel. The personal care composition can be applied to any portion of the body such as, for example, the lips, hands, neck, ears, stomach, back, arms, legs, face, and feet. The personal care composition according to a method of the present invention can protect against UVA, UVB, or both types of UV radiation.

EXAMPLES

Semiconductor nanocrystals may be prepared using any known method of semiconductor nanocrystal preparation. One such method is described below. Additionally, semiconductor nanocrystals suitable in the present invention can be otherwise obtained (Evident Technologies, Troy, N.Y.). Further, the exemplary methods are described with respect to the preparation of zinc selenide semiconductor nanocrystal however many other nanocrystals may be used for the present invention including but not limited to ZnS, ZnO, CdS, SrS, SrSe, GaN, InN, GaP, AlP or derivatives thereof.

Example 1

0.82 g (10 mmol) ZnO, 20 mL oleic acid, 20 mL octadecene are heated under $N_2$ at 280° C. with rapid stirring for ~1 hour to fully dissolve ZnO resulting in zinc oleate. A slurry of 0.63 g (8 mmol) Se powder in octadecene is injected into the reaction mixture at 280° C. Initially the reaction turns deep amber color then lightens to pale yellow. The yellow color deepens and intensifies as the particle size grows larger. The temperature setting after injection of Se affects the rate of particle growth. The particle growth is tracked by monitoring the evolution of the absorption spectrum. After reaching a desired size, the growth is halted by removing the heat source to cool the reaction. The ZnSe product is isolated by precipitation with polar solvents, such as acetone and methanol and centrifugation to remove the reaction supernatant. The powder product is redispersed in an organic solvent such as toluene or chloroform, and this solution is centrifuged to remove unreacted Se debris. The ZnSe is precipitated a second time, and the isolated product is dispersed directly into capric/caprylic triglyceride using vigorous stirring, shaking, or other suitable mixing techniques. The product could also be dissolved into the capric/caprylic triglyceride. At loading levels approximately 25% w/w the mixture has been found to be characteristic of a solution. At loading levels approximately 50% w/w the mixture has been found to be characteristic of a dispersion.

Although the zinc precursor for the above described preparation is ZnO, many zinc precursors including but not limited to zinc acetate, zinc acetylacetonate, zinc chloride, zinc nitrate. Additionally, although the coordinating ligand for the above described synthesis is oleic acid other coordinating ligands including but not limited to long chain ($n \geq 4$) hydrocarbons containing at least one of the following functional groups; carboxylic acid, amine, phosphine, phospine oxide and phosphonic acid.

The personal care material prepared above may be applied as existing personal care products. For example, by dispersing or dissolving the semiconductor nanocrystals prepared above in a skin lotion or a sun tan lotion, the personal care product may be applied directly to an area of skin such as the skin lotion or sun tan lotion in which the semiconductor nanocrystal is dispersed or dissolved.

Example 2

ZnSe made according to the above described procedure is prepared and dissolved in toluene. Next, 99 g of polystyrene is dissolved in 1.0 L of toluene at 110.6° C. (boiling). After the polystyrene is dissolved, 1.0 g of ZnSe semiconductor nanocrystals are added to the solution and mixed. Next, the toluene is evaporated by heating the solution to 110.6° C. until the total volume is reduced to approximately 500 mL. The solution is then be poured into a 9×13 inch Pyrex tray, and placed in a fume hood overnight to allow for most of the solvent to evaporate. The remaining solvent is removed using a vacuum oven (50° C.). This results in the formation of a polymer/semiconductor nanocrystal solid. This resulting solid is then be processed in a blender and, finally, micronized to the desired size.

The personal care material prepared above may be applied as existing personal care products. For example, by dissolving the semiconductor nanocrystals prepared above in a skin lotion or a sun tan lotion, the personal care product may be applied directly to an area of skin such as the skin lotion or sun tan lotion in which the semiconductor nanocrystal is dispersed. The resulting solid substantially absorbs both UV A and UV B light and due to the size of the particles would not cause whitening.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Further, it is appreciated that although a number of problems and deficiencies may be identified above with respect to the prior cosmetic ingredients, each embodiment of the present invention may not solve each problem identified in the art. Additionally, to the extent a problem identified in the art or an advantage of the present invention is not cured, solved or lessened by the claimed invention, the solution to such problems or the advantage identified above should not be read into the claimed invention. Furthermore, all references cited herein are incorporated by reference in their entirety.

What is claimed is:

1. A personal care composition comprising:
   a personal care ingredient; and
   a semiconductor nanocrystal dispersed or dissolved in the personal care ingredient, the semiconductor nanocrystal having a diameter between one and twenty nanometers.

2. The personal care composition of claim 1, wherein the semiconductor nanocrystal is ZnSe, ZnS, ZnO, CdS, SrS, SrSe, GaN, InN, GaP, AlP or derivatives thereof.

3. The personal care composition of claim 2, wherein the semiconductor nanocrystal is ZnSe.

4. The personal care composition of claim 1, wherein, the personal care ingredient is fatty acids, fatty esters, waxes, oils, triglycerides, long chain alcohols, silicones, or any combination thereof.

5. The personal care composition of claim 1, wherein the personal care composition is a hair conditioner, moisturizer, sun tan lotion, lipstick, or a hair gel.

6. The personal care composition of claim 1, wherein the personal care composition substantially absorbs ultraviolet light.

7. A personal care composition comprising:
   a personal care ingredient; and
   a matrix material comprising a semiconductor nanocrystal having a diameter between one and twenty nanometers, wherein the matrix material is dispersed or dissolved in the personal care ingredient.

8. The personal care composition of claim 7, wherein the semiconductor nanocrystal is ZnSe, ZnS, ZnO, CdS, SrS, SrSe, GaN, InN, GaP, or AlP.

9. The personal care composition of claim 8, wherein the semiconductor nanocrystal is ZnSe.

10. The personal care composition of claim 7, wherein the personal care ingredient is fatty acids, fatty esters, waxes, oils, triglycerides, long chain alcohols, silicones, or any combination thereof.

11. The personal care composition of claim 7, wherein the personal care composition is a hair conditioner, moisturizer, sun tan lotion, lipstick, or a hair gel.

12. The personal care composition of claim 7, wherein the personal care composition substantially absorbs ultraviolet light.

13. The personal care composition of claim 7, wherein the matrix material is a polymer.

14. A method of manufacturing the personal care composition of claim 1 comprising:
    providing a personal care ingredient; and
    dissolving or dispersing a semiconductor nanocrystal in the personal care ingredient.

15. A method of manufacturing the personal care composition of claim 7 comprising:
    providing a personal care ingredient;
    providing a matrix material comprising a semiconductor nanocrystal; and
    dissolving or dispersing the matrix material in the personal care ingredient.

16. A method of protecting at least a portion of a body against ultraviolet radiation, the method comprising:
    applying a personal care composition to at least a portion of the body, wherein the personal care composition comprises a personal care ingredient and a semiconductor nanocrystal, the semiconductor nanocrystal having a diameter between one and twenty nanometers.

* * * * *